United States Patent
Purcell et al.

(10) Patent No.: US 7,717,226 B2
(45) Date of Patent: May 18, 2010

(54) HEARING PROTECTION CAP

(75) Inventors: Ricky Wayne Purcell, Alpharetta, GA (US); Cristine E. Schulz, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 120 days.

(21) Appl. No.: 12/070,810

(22) Filed: Feb. 20, 2008

(65) Prior Publication Data

US 2009/0205900 A1    Aug. 20, 2009

(51) Int. Cl.
*H04R 25/02* (2006.01)
*H04R 25/00* (2006.01)

(52) U.S. Cl. ................ 181/129; 381/372

(58) Field of Classification Search ......... 181/129, 181/136, 290; 381/72, 372, 371; 2/423, 2/209; 128/864, 865, 867
See application file for complete search history.

(56) References Cited

U.S. PATENT DOCUMENTS

| | | | |
|---|---|---|---|
| 428,511 A | 5/1890 | Moore | |
| 2,597,508 A | 5/1952 | Majewski | |
| 2,684,067 A * | 7/1954 | Lienard | 128/866 |
| 2,712,134 A | 7/1955 | Cyr | |
| 2,757,247 A * | 7/1956 | Gavreau | 181/256 |
| 2,782,423 A | 2/1957 | Simon et al. | |
| 2,802,214 A | 8/1957 | Hanks | |
| 3,005,203 A * | 10/1961 | Aileo | 2/423 |
| 3,112,493 A | 12/1963 | Greenberg | |
| 3,456,263 A * | 7/1969 | Aileo | 2/423 |
| 3,593,341 A | 7/1971 | Aileo | |
| 3,728,741 A * | 4/1973 | Lepor | 2/209 |
| 3,795,014 A | 3/1974 | Simpson et al. | |
| 3,841,325 A | 10/1974 | Pickard | |
| 3,908,200 A * | 9/1975 | Lundin | 2/209 |
| 3,944,018 A * | 3/1976 | Satory | 181/175 |
| 4,087,653 A * | 5/1978 | Frieder et al. | 379/430 |
| 4,103,359 A * | 8/1978 | Rieppel et al. | 2/8.1 |
| 4,134,153 A | 1/1979 | Voorhees | |

(Continued)

FOREIGN PATENT DOCUMENTS

DE     298 12 652 U1    3/1999

(Continued)

OTHER PUBLICATIONS

American Society for Testing Materials (ASTM) Designation: E1050-98, "Standard Test Method for Impedance and Absorption of Acoustical Materials Using A Tube, Two Microphones and A Digital Frequency Analysis System," pp. 1-11, published Aug. 1998.

(Continued)

*Primary Examiner*—Edgardo San Martin
(74) *Attorney, Agent, or Firm*—Denise Stoker; Nathan P. Hendon

(57) ABSTRACT

The present invention relates to an ear cap intended for use as hearing, the ear cap having a sound-reflecting outer shell and a liner of sound absorption materials. The ear cap is characterized by at least one sound-reflecting and vibration-damping weight element arranged on or within the sound absorption liner to at least partly block an audio mode of vibration that would have existed in the cap in the absence of the weight element.

17 Claims, 3 Drawing Sheets

U.S. PATENT DOCUMENTS

| | | | | |
|---|---|---|---|---|
| 4,156,118 A | * | 5/1979 | Hargrave | 381/372 |
| 4,459,707 A | | 7/1984 | Stallings | |
| 4,572,323 A | * | 2/1986 | Randall | 181/129 |
| 4,614,487 A | | 9/1986 | Csiki | |
| 4,658,931 A | | 4/1987 | Curry | |
| 4,674,134 A | * | 6/1987 | Lundin | 2/209 |
| 4,771,454 A | * | 9/1988 | Wilcox, Jr. | 379/430 |
| 4,905,322 A | * | 3/1990 | Aileo et al. | 2/209 |
| 4,930,520 A | | 6/1990 | Liverani | |
| 5,020,163 A | * | 6/1991 | Aileo et al. | 2/209 |
| 5,023,955 A | | 6/1991 | Murphy, II et al. | |
| 5,224,495 A | | 7/1993 | Robinson | |
| 5,241,971 A | * | 9/1993 | Lundin | 128/864 |
| 5,243,709 A | | 9/1993 | Sheehan et al. | |
| 5,420,381 A | | 5/1995 | Gardner, Jr. et al. | |
| 5,551,090 A | * | 9/1996 | Thompson | 2/209 |
| 5,815,842 A | | 10/1998 | Hiselius | |
| 5,826,582 A | | 10/1998 | Sheehan et al. | |
| 5,898,945 A | | 5/1999 | Weiser | |
| 5,911,314 A | | 6/1999 | Urella et al. | |
| 5,924,138 A | | 7/1999 | Baisden | |
| 5,970,160 A | | 10/1999 | Nilsson et al. | |
| 6,055,672 A | | 5/2000 | Natvig | |
| 6,151,717 A | | 11/2000 | Lindgren et al. | |
| 6,154,890 A | * | 12/2000 | Deopuria et al. | 2/423 |
| 6,353,938 B1 | | 3/2002 | Young | |
| 6,386,314 B1 | | 5/2002 | Sheehan et al. | |
| 6,427,800 B1 | | 8/2002 | Hiselius et al. | |
| 6,702,817 B2 | | 3/2004 | Beger et al. | |
| 6,826,287 B2 | | 11/2004 | Myers | |
| 6,832,663 B2 | | 12/2004 | Warring et al. | |
| 7,024,013 B1 | | 4/2006 | Van Dam et al. | |
| 7,058,985 B2 | | 6/2006 | Tanaka | |
| 2005/0273910 A1 | | 12/2005 | Cozens et al. | |
| 2005/0283882 A1 | | 12/2005 | Berger et al. | |
| 2007/0044205 A1 | | 3/2007 | Sato et al. | |
| 2007/0143907 A1 | | 6/2007 | Hansson et al. | |
| 2008/0263749 A1 | * | 10/2008 | Leong et al. | 2/209 |

FOREIGN PATENT DOCUMENTS

| | | |
|---|---|---|
| EP | 0 993 815 A2 | 4/2000 |
| EP | 0 751 720 B1 | 5/2000 |
| GB | 2 320 885 A | 7/1998 |
| JP | 06-007396 A | 1/1994 |
| WO | WO 81/02515 A1 | 9/1981 |
| WO | WO 97/48296 A1 | 12/1997 |
| WO | WO 98/31314 A1 | 7/1998 |
| WO | WO 03/010993 | 2/2003 |
| WO | WO 2004/049752 A1 | 6/2004 |
| WO | WO 2005/122982 A1 | 12/2005 |
| WO | WO 2006/036111 A1 | 4/2006 |

OTHER PUBLICATIONS

Patent Cooperation Treaty Search Report from the International Search Authority, International Application No. PCT/IB2009/050382 dated Oct. 9, 2009.

* cited by examiner

HEARING PROTECTION CAP

BACKGROUND OF THE DISCLOSURE

The present invention relates to devices for covering an ear, and more particularly to such devices that include a vibration damper for sound optimization such as noise reduction.

Hearing protection is essential for workers in high or repetitive noise environments. If a person works in more than one area, perhaps a warehouse and a manufacturing floor, two different levels of hearing protection may be needed. For example, on a relatively high-noise manufacturing floor, a heavy set of ear caps (also known as "ear muffs") are most suitable. In the warehouse environment, a much lighter set of ear caps may be adequate. However, comfort is affected by the size and weight of a cap-style hearing protection device. Typically, the bulkier the ear caps, the less comfortable they are for the wearer. When a person is only provided with the heavier set of ear caps, he or she may forego wearing them in the warehouse or other environment where the noise level is not as high. Over time, this can lead to hearing damage or loss. Of course, when the person is provided with two sets of ear caps, each customized for a particular noise level, the person is more likely to wear ear caps in each setting. Unfortunately, this means that a person or company needs to spend more money for the additional ear caps.

To keep costs as low as possible, it is desirable to use a previously tooled design in the manufacture of ear caps, and where possible, use an ear cap that has the same outer shell or housing for each different level of sound attenuation desired. However, there remains the problem of cost-effectively customizing a previously tooled ear cap design.

Accordingly, while various types of ear protection devices exist, there remains a clear need for an ear protection device that can be customized, yet provided at a relatively low cost to a consumer. In particular, there remains a need for a product that is improved with respect to the sound attenuation performance of a previously tooled ear cap.

SUMMARY OF THE INVENTION

The present invention includes a hearing protection cap set, wherein each cap has a shell member with an inner surface and an opposite exterior surface. The shell has an inner layer which includes a flexible inner layer disposed against the inner surface of the shell member, and a flexible facing layer. The facing layer has an ear-facing surface and an opposite attachment surface. The attachment surface is disposed against the hidden layer. A weight element is positioned between the facing layer and the hidden layer.

Another aspect of the invention is a hearing protection cap including a shell member having an inner surface defining a cavity and an opposite exterior surface. A hidden layer is disposed within the shell member cavity against the inner surface of the shell member. A facing layer has an ear-facing surface and an opposite attachment surface. The attachment surface is disposed within the shell member cavity against the hidden layer. A flexible weight element is positioned between the facing layer and the hidden layer.

In yet another aspect of the invention there is a method of improving the sound attenuation of a hearing protection cap having a cap shell having an inner surface defining a cavity. The method steps include the lining of the cavity with an inner layer of sound absorption material, and the attachment of a weight element to an ear-facing surface of the inner layer.

The inventive cap may have one or more of advantages over prior art hearing protection caps. Some exemplary benefits are as follows.

First, the inventive cap allows entities to improve the sound attenuation of pre-existing cap-shell designs available from a contract manufacturer or other sources. By introducing a relatively thin and possibly flexible weight element with the sound absorbing material(s) lining the cap shell, the sound attenuation is improved without sacrificing comfort and without having to alter the design of the cap shell, which can require expensive retooling.

Second, use of weight elements provides the advantage that the sound attenuation can be increased with retained or even reduced bulk/size/volume of the cap, especially of the cap shell. Thinner cap shells, which are made possible by the invention, result not only in lower costs of material, but also in greatly shortened cooling times in the injection molding process. The cooling time is the time that dominates production. By shortening cooling time, the machine cost per cap ratio is reduced. This results in more economical production costs and shorter times of delivery.

Third, identical cap shells may be used for several different models of ear caps, each providing different levels of sound attenuation. A reduction in the number of cap shell models (SKU's) will further reduce manufacturing costs.

Fourth, by arranging weight elements inside a sound absorbing material, resonances in the cap shell can be modified to improve the sound attenuation capability of the cap shell.

Fifth, a marketer of ear caps can more easily differentiate its brand of ear caps from other ear caps produced by the same contract manufacturer.

Other advantages and features will be in part apparent and in part pointed out hereinafter.

BRIEF DESCRIPTION OF THE DRAWINGS

Corresponding reference characters indicate corresponding parts throughout the drawings.

DETAILED DESCRIPTION

The present disclosure generally relates to devices for covering an ear, and more particularly to such devices that are used for sound optimization, such as noise reduction. Advantageously, the caps of the present disclosure have good sound-attenuating properties, and can be manufactured by a contract manufacturer without creating new machine tooling for the cap shell injection mold.

Figure 1:
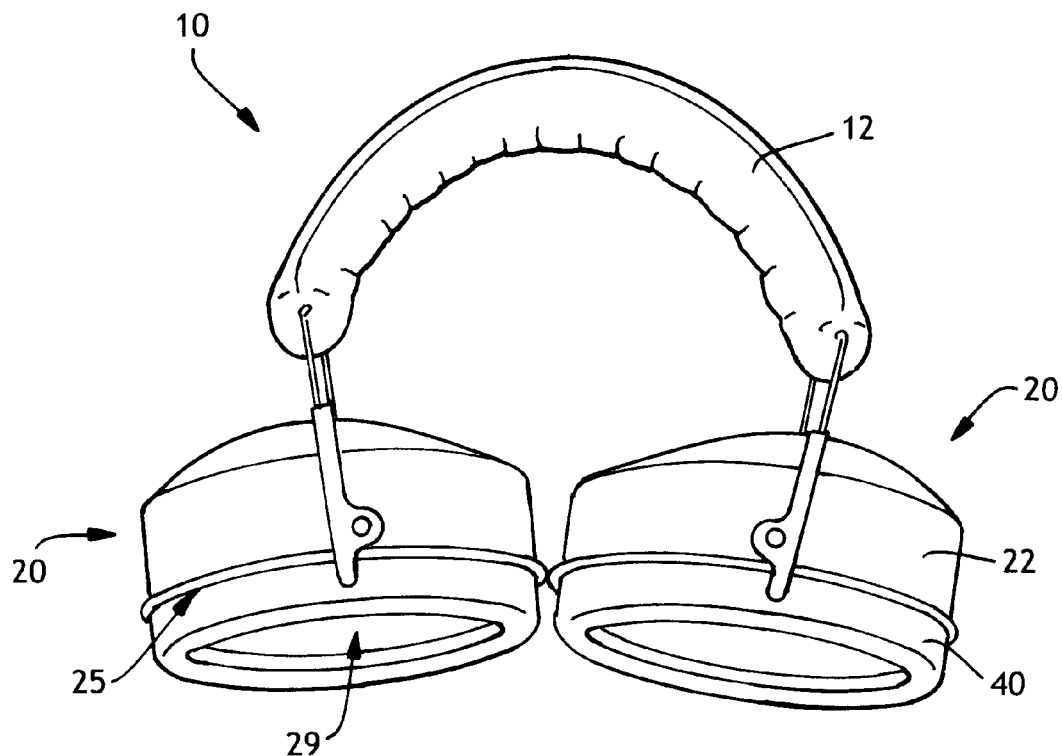
FIG. 1 is a side perspective view in which two hearing protection caps of the present invention are joined by a head band.
Figure 2:
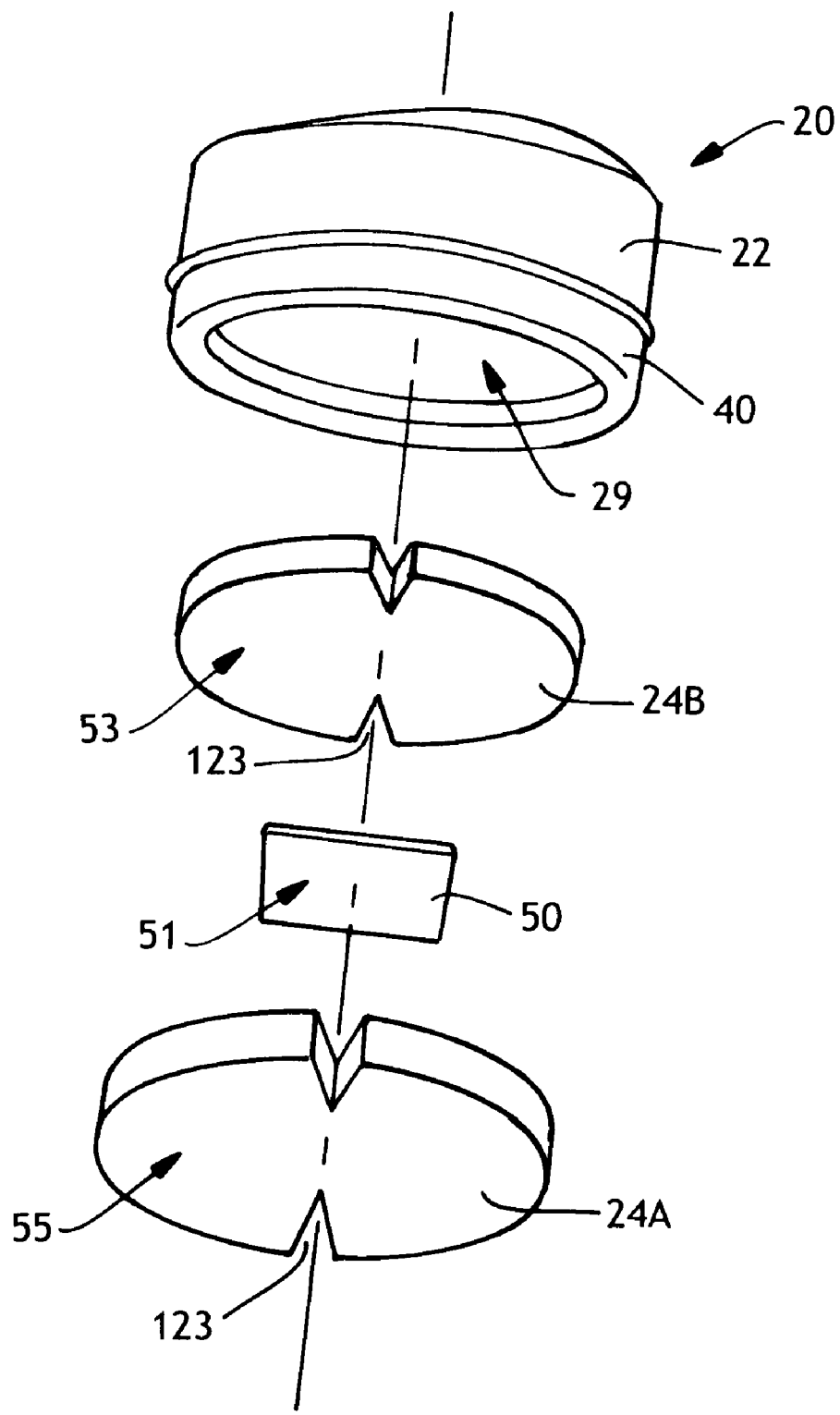
FIG. 2 is a semi-exploded view of one of the caps shown in FIG. 1.
Figure 3:
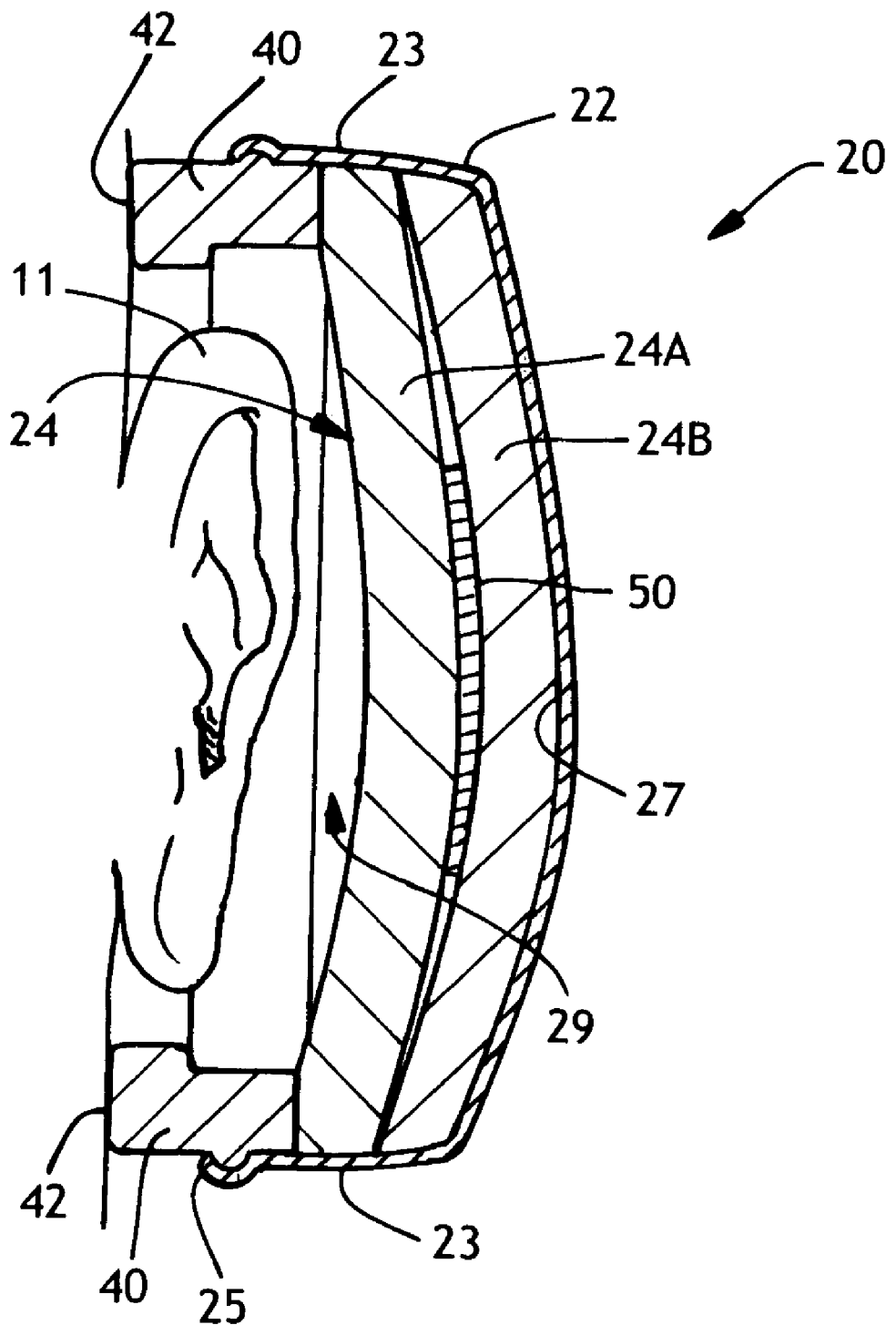
FIG. 3 is a side cross-section of another embodiment of a cap of the present invention, having a hidden layer and facing layer that are approximately the same size.

Referring now to the drawings and in particular FIG. 1, there is depicted a hearing protection cap assembly 10 made with a pair of ear caps 20 according to the present disclosure, connected together with a head band 12 as is known in the art. As seen in FIGS. 2 and 3, each hearing protection cap 20 comprises an outer shell 22 defining a generally oval or circular shaped cavity 29 for covering a user's external ear 11. The outer shell may be domed, as illustrated in the figures, flat (not shown), or any other suitable shape. An inner layer 24 that includes at least one type of sound absorbing material lines the cavity 29. The inner layer 24, as described below, is desirably a composite of two layers, 24A and 24B, between which a sound-reflecting/vibration-damping weight element 50 is located. A sealing member 40 is used to seal the shell 22 to the head portion surrounding the user's ear 11 (see FIG. 3).

The term "cap" or "ear cap" means a single ear covering unit which is adapted to cover a human user's ear. A hearing protection "cap set" is defined as a pair of ear caps. A pair of caps 20 may be connected to a headband 12 or other devices known in the art. In the alternative, each cap 20 may be selectively attachable to a user's ear as shown and described in patent Ser. No. 11/742,492 filed on Apr. 30, 2007 by Leong et al., incorporated herein to the extent it is consistent with the present invention.

An ear cap 20 oscillates or vibrates in resonance with an incoming sound wave when the cap has a natural frequency matching a frequency of the incoming sound wave. An audio "mode" of vibration is defined as a resonance peak in a sound frequency spectrum. A cap usually has a plurality of such modes of vibration along the audible frequency spectrum. At a frequency below about 250 Hz, the sealing member 40 of the cap is usually capable of producing a mode of vibration by acting as a resonance spring. Only at higher frequencies, above about 1 kHz, can modes of vibration start to occur within the cap shell. In each mode of vibration above about 1 kHz, the cap shell has a certain number of vibration nodes and antinodes distributed across its surface. Vibration "nodes" are defined as points, lines or surfaces in an oscillating system, in which the vibrations are minimal, while "antinodes" involve the opposite, i.e. points, lines, or surfaces, in which the vibrations are at their maximum. Using a weighted element 50 to block an audio mode of vibration in a cap changes its resonance properties so that a resonance peak in the sound frequency spectrum is decreased or eliminated.

The outer shell 22, the inner layer 24, and the weight element 50 of the sound attenuating cap 20 advantageously work in combination to attenuate sound. More specifically, the outer shell 22 and the weight element 50 each comprise a sound-reflecting material that reflects sound away from the ear, while the inner layer 24 of the sound attenuating cap 20 comprises a sound absorbing material for absorbing sound that penetrates through the outer shell 22. Weight element 50 also functions as a vibration damping device. Sound energy that is not reflected by the outer shell 22 and the weight element 50 can be absorbed by the inner layer 24 of the sound attenuating cap, and reflected or dampened or a combination thereof by the weight element 50.

The sound attenuation efficiency of the sound-reflecting and sound-absorbing materials used to form the sound attenuating cap can be expressed in terms of their sound absorption coefficient. The sound absorption coefficient of a material can have a value between 0 and 1, with 0 representing no sound absorption and 100% sound reflection, and 1 representing 100% sound absorption and no sound reflection. The sound absorption coefficient can be expressed as: $\alpha = Ia/Ii$, wherein Ia is the sound intensity absorbed (Watts per square meter (W/m2)) and Ii is the incident sound intensity (W/m2). Methods for measuring sound absorption coefficients of materials are known and include, for example, ASTM E1050 "Standard Test Method for Impedance and Absorption of Acoustical Materials Using a Tube, Two Microphones and a Digital Frequency Analysis System." While the sound absorption coefficient of a material may vary with the frequency of the sound, advantageously, the sound reflecting materials of the outer shell 22 and weight element 50 are capable of reflecting or dampening both high and low frequency sound, while the sound absorbing materials of the inner layer 24 are capable of absorbing both high and low frequency sound.

A variety of sound reflecting materials may be used to create the outer shell. Examples of suitable sound reflecting materials include, for example, mass loaded polymer, high density plastic, metals, woods, and combinations thereof. Specific examples of suitable plastics include polycarbonate, high density polyethylene, and polyvinyl chloride, and the like. Specific examples of metals include lead, steel, brass, bronze, and the like. Specific examples of woods include birch, oak, larch, and the like. Desirably, the outer shell 22 of the sound attenuating cap 20 comprises a relatively high-mass material.

The edges of the outer shell 22 and inner layer 24 of the sound attenuating cap 20 terminate in a rim portion 23, which encircles the ear. The rim portion 23 has a width defined by an inner circumference 30, which runs along the interior side (cavity-facing side) of the inner layer 24, and an outer circumference 32, which runs along the outer surface of the outer shell 22. In an alternate embodiment, the outer shell 22 may extend around the rim portion 23, covering all or a portion of the inner layer 24 along the rim portion. In another embodiment (not shown), a separate component covers a portion of layer 24. The separate component can be adhered, fastened, or snap-fitted to shell 22.

Desirably, the sound reflecting materials that make up the outer shell may reflect at least about 60%, and more desirably, at least about 80% of sound energy over the frequency range of from about 800 Hz to about 10,000 Hz, thus having a sound absorption coefficient of no more than about 0.4 and more desirably no more than about 0.2 over the frequency range of from about 800 Hz to about 10,000 Hz. In one embodiment, the sound attenuating cap 20 desirably has an overall Noise Reduction Rating of at least about 8 dB, and more desirably from about 17 dB to about 30 dB.

In addition to sound attenuating capability, other factors that may be considered in selecting the combination of materials for the inner layer 24 and outer shell 22 include the desired weight and size of the sound attenuating cap 20, as well as cost of making the cap. For instance, depending on the type of material selected to form the outer shell 22, the weight element 50, and the inner layer 24; the thickness of the sound attenuating cap may vary. In one embodiment, the outer shell 22 typically has a thickness of at least about 1 millimeter, and more typically has a thickness of from about 1 millimeter to about 10 millimeters, desirably from about 2 millimeters to about 5 millimeters.

As noted above, the inner layer 24 is generally constructed from sound absorbing materials that diminish sound which penetrates outer shell 22, thus improving the sound attenuating effects of cap 20. A variety of sound absorbing materials may be used in the inner layer 24. Each such material can flex enough so that it can be packed into the cavity 29 and function as a cap shell liner. Examples of suitable sound absorbing materials include, for example, glass fibers, fibrous mineral wool, a foam, and the like. Other suitable sound absorbing materials include polyolefin fibers, polyurethane foams, and the like. Desirably, the inner layer 24 is made from a flexible foam material, either open cell foam and/or semi-open cell foam.

Desirably, to enable the placement of weight element 50 (or multiple weight elements 50) within the inner layer 24, the inner layer 24 is a composite of two layers of material, designated as layers 24A and 24B, see FIG. 2. Generally, layer 24A, the "facing layer," defines the inner surface of the hearing protection cap 20 that faces the ear of the user, and possibly makes contact therewith. Layer 24B, the "hidden layer" is disposed adjacent to the outer shell 22.

The layers 24A and 24B may be made from identical materials, or from different materials. In the alternative, the layers 24A and 24B may be made from like materials that exhibit different physical properties, such as different density or stiffness.

As can be seen in FIG. 2, the layers 24A and 24B may have the same shape yet different sizes. By making hidden inner layer 24B smaller than the contact inner layer 24A, it may be easier to pack the layers into the shell 22 to minimize or eliminate any air gaps between the layers. However, it is contemplated that the layers 24A and 24B may be of the same size, as seen in FIG. 3. The layers 24A and 24B may be secured together by disposing an adhesive between the layers. In addition, the layers 24A and 24B, to the extent that they make contact with the inner surface 27 of shell 22, may be adhered to the shell by an adhesive.

The inner layer 24 typically has total thickness of at least about 5 millimeters, and more typically has a thickness of from about 5 millimeters to about 40 millimeters, desirably from about 5 millimeters to about 20 millimeters. Desirably, the materials used to form the outer shell 22 and inner layer 24 are selected so that the thickness of the sound attenuating cap 20 (e.g., along the rim portion 23) is from about 15 millimeters to about 30 millimeters.

The shapes of layers 24A and 24B may also be identical as shown. However, the shape of each layer will ultimately depend upon the cavity shape defined by shell 22. In the embodiment of FIG. 2, notches 123 may be placed along the outer edge of each layer 24A and 24B so that they can more easily conform to the domed shape of shell 22.

In another embodiment of the present invention, there is only a unitary layer 24, and the weight element is disposed on an ear-facing surface thereof so that it is visible to the wearer. In this case, the weight element 50 may have an aesthetic shape or bear a logo or other indicia.

Overall, the choice of sound absorbing materials for use in the inner layer 24 may vary depending on the type of sound reflecting material used in the outer shell 22 and weight element 50, but is desirably selected so that the sound attenuating cap (i.e., the combination of the outer shell 22, the weight element 50, and the inner layer 24 of the sound attenuating cap 20) attenuates from about 8 dB to about 33 dB over the frequency range of from about 65 Hz to about 8,000 Hz. Desirably, the sound absorbing materials that make up the inner layer 24 will absorb at least about 60% and more desirably at least about 80% of sound energy over the frequency range of from about 800 Hz to about 10,000 Hz, thus having a sound absorption coefficient of at least about 0.6 and more desirably at least about 0.8 over the frequency range of from about 800 Hz to about 10,000 Hz.

The weight element 50 is formed into a sheet-like member to fit within the layer 24, such as between layers 24A and 24B. Weight element 50 may be glued to layer 24A and/or 24B using different types of glue or adhesive according to the properties of the materials of which the layer 24 and the weight element 50 are made. The components may also be joined by adhesive tape.

In one embodiment, weight element 50 is formed by extruding into a sheet a blend of metal (e.g., it could be a heavy metal or other metal) and polymer such as vinyl. Desirably, this results in a flexible weight member 50. In one embodiment of the present invention, the mass-loaded vinyl may have a thickness of 1 mm to 2.54 mm, and a basis weight of about 2.5 kg/m2 to about 5 kg/m2 (0.05 to 1 lbs/ft2). A suitable mass-loaded vinyl can be obtained from McMaster-Carr, Atlanta, Ga., models STL 20 or 26. However, it is contemplated that a sheet or disc of metal or metal alloy may be used instead of the polymer/metal composite. Further, it is contemplated that the weight element may be injection molded, cast, stamped, or made by any suitable method.

In another embodiment of the present invention, the weight element 50 has a density which is greater than the density of the cap shell 22. As a result, effective resonance absorption can be provided with a relatively small volume of the weight element 50. The difference in density can be provided by the weight element 50 being made in part or in whole of a heavy material, such as metal, zinc (density of about 7.1 g/m$^3$), a zinc alloy, iron (density of about 7.9 g/m$^3$), or lead (density of about 11.4 g/m$^3$), while the cap shell 22 may be about 2 g/m$^3$ or less. To have a more significant effect on resonance absorption, the weight member may have a mass or weight of at least 5% of the shell mass.

The weight element 50 may be any shape, but a rectangular shape is desirable for a mass-loaded vinyl because it can be cut from larger sheets with little waste. However, it is contemplated that the weight element could be round, oval, or any other suitable shape. If a shape becomes too elongated, it may less effectively serve to reflect sound waves in a desired frequency range.

Figure 2A:
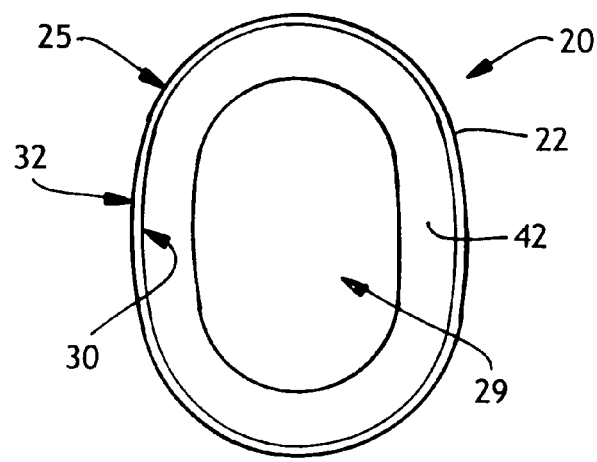
FIG. 2A is a bottom elevation of one of the caps shown in FIG. 1.

The hearing protection has a footprint area defined by the circumference of the cap 20, the circumference located at the edge 25 of the cap 20 nearest the sealing member 40, see FIGS. 1 and 2A. Desirably, the weight element 50 defines an area that is at least 50 percent less than the footprint area, or in another embodiment, an area that is at least 75 percent less than the footprint area.

Generally, the weight element 50 has an area that is less than an area defined by the inner layer 24. Specifically, as seen in FIG. 2, weight element 50 may have a surface area 51 that is less than the outward surface area 55 of layer 24A, or less than the outward surface area 53 of layer 24B. It is noted that each surface area 51, 53 and 55 lies in a single plane.

As can be seen with reference again to FIGS. 1 and 2, the hearing protection cap 20 of the present disclosure may further comprise a sealing member 40. The sealing member 40 has a surface 42 for being placed against a portion of the user's head. More specifically, the sealing member 40 provides a seal between the sound attenuating cap 20 and the head portion around the ear which contacts the cap 20. Advantageously, the presence of the sealing member 40 may reduce the amount of sound energy that penetrates between the edges of the cap and the user's head when the cap is worn. The sealing member 40 may also act as a cushion, providing a softer and more comfortable surface for being placed against a portion of the user's head when the cap is in use.

Typically, the sealing member 40 is disposed adjacent to the rim portion 23 of the sound attenuating cap 20. The sealing member 40 may be attached to the sound attenuating cap 20 using any suitable means, such as, for example, adhesives. Examples of suitable adhesives include silicone adhesives, hydrogel adhesives, and the like.

The sealing member 40 may comprise a cushioning material, such as a polyurethane foam with vinyl skin, ethylene-vinyl acetate, silicone rubber, ethylene propylene rubber, and the like. Alternately or in addition, the sealing member 30 may comprise an adhesive material, such as, for example, a contact adhesive, such as a pressure-sensitive adhesive suitable for long-term skin contact, a silicone adhesive, a hydrogel adhesive, and the like.

In the embodiment shown in FIG. 1, the weight element 50 is positioned within inner layer 24 as previously described. At higher frequencies, from about 1 kHz upwards, noise vibrations occur in precisely the cap shell 22 of the cap 20. By arranging the weight element 50 within the cavity of cap 20, resonances within the cap can be modified at certain frequencies of the incoming sound.

To determine the optimal position of weight element 50 within layer 24, it is possible to use one of two methods: (1) trial and error, or (2) finding where antinodes occur within the cap for select modes of vibrations, and arranging weight elements 50 to coincide therewith.

In both methods, sound attenuation is measured in the cap 20 with and without weight elements 50, and comparisons are made. One method of measuring sound attenuation within cap 20 is performed in a sound-isolated environment as follows. First, arrange microphones in the ears of an individual or on an artificial head. Using a loud speaker in the vicinity of the cap 20, create a noise at a first frequency along the audible frequency spectrum. Measure the sound volume received by the microphone at the first frequency without the ear cap 20 covering the microphone to establish a reference. Place the ear cap 20 over the microphone so that the seal member forms a seal against the head. Again measure the sound volume received by the microphone at the first frequency. Repeat the measurement at the first frequency after placing a weight element 50 in the inner layer 24. Compare the results between different weight element placement and weightings.

In the second method, cap antinodes are determined and weight elements are disposed in the inner layer to cover the antinodes. The result of the arrangement can in the same way as stated above be evaluated by preparing an attenuation spectrum chart. Finding where antinodes occur can be made by a modal analysis, such as finite element or vibration analysis as is known in the art of acoustics.

A cap 20 usually has a plurality of modes of vibration or resonance peaks along the frequency spectrum. In each such mode of vibration, the cap has a predetermined number of vibration nodes and antinodes distributed over the cap shell. Arranging a weight element 50 in the center of an antinode of the cap 20 (an antinode that occurs at a certain mode of vibration) blocks not just the current mode of vibration but also other modes of vibration, whose antinodes coincide with the antinode of the current mode of vibration.

Having described the disclosure in detail, it will be apparent that modifications and variations are possible without departing from the scope of the disclosure defined in the appended claims.

When introducing elements of the present disclosure or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description and shown in the accompanying drawings shall be interpreted as illustrative and not in a limiting sense.

The invention claimed is:

1. A hearing protection cap set, each cap comprising:
   a shell member having an inner surface and an opposite exterior surface;
   an inner layer comprising a flexible hidden layer disposed against the inner surface of the shell member, and a flexible facing layer having an ear-facing surface and an opposite attachment surface, the attachment surface disposed against the hidden layer; and
   a weight element positioned between the facing layer and the hidden layer,
   wherein the shell member defines a footprint having a footprint area, and the weight element defines an area that is at least 50 percent less than the footprint area.

2. The hearing protection cap set of claim 1 wherein the shell member forms a cavity defined by the inner surface.

3. The hearing protection cap set of claim 1 wherein the hidden layer is a first sound absorbing material.

4. The hearing protection cap set of claim 3 wherein the facing layer is a second sound absorbing material, which may be made of a material similar or different than the first sound absorbing layer.

5. The hearing protection cap set of claim 4 wherein the first sound absorbing layer and the second sound absorbing layer are of an identical material.

6. The hearing protection cap set of claim 1 wherein the facing layer and the hidden layer are each made of a foam sound absorbing material.

7. The hearing protection cap set of claim 1 wherein the weight element comprises a polymer having a first specific gravity, wherein the polymer is impregnated with a material having a second specific gravity that is greater than the first specific gravity.

8. The hearing protection cap set of claim 7, wherein the weight element comprises a composite sheet of vinyl and lead.

9. The hearing protection cap set of claim 1 wherein the shell defines a footprint having a footprint area, and the weight element defines an area that is at least 75 percent less than the footprint area.

10. A hearing protection cap comprising:
    a shell member having an inner surface defining a cavity and an opposite exterior surface;
    a hidden layer disposed within the shell member cavity against the inner surface of the shell member;
    a facing layer having an ear-facing surface and an opposite attachment surface, the attachment surface disposed within the shell member cavity against the hidden layer; and
    a flexible weight element positioned between the facing layer and the hidden layer,
    wherein the shell member defines a footprint having a footprint area, and the weight element defines an area that is at least 50 percent less than the footprint area.

11. The hearing protection cap of claim 10 wherein the flexible weight element comprises a polymer and a metal.

12. The hearing protection cap of claim 11 wherein the metal comprises lead.

13. The hearing protection cap of claim 10 wherein the hidden layer and the facing layer comprise an identical material.

14. The hearing protection cap of claim 10 wherein the weight element is adhesively attached to the hidden layer, the facing layer, or both.

15. A method of improving the sound attenuation of a hearing protection cap comprising a cap shell having an inner surface defining a cavity, the method comprising the steps of:

lining the cavity with an inner layer of sound absorption material;
co-extruding a polymer and a metal into a sheet;
forming a weigh element from the sheet;
sizing the weight element so that it has an area that is less than an area defined by the inner layer; and
attaching the weight element to an ear-facing surface of the inner layer.

16. The method of claim 15 comprises the step of positioning a second layer over the inner layer and the weight element.

17. The method of claim 15 further comprising the step of positioning the weight element on the inner layer such that it coincides with a cap antinode.

\* \* \* \* \*